United States Patent
Reed

(12) 
(10) Patent No.: US 7,071,295 B2
(45) Date of Patent: Jul. 4, 2006

(54) SIGNAL FOR TARGETING MOLECULES TO THE SARCO(ENDO)PLASMIC RETICULUM

(75) Inventor: Thomas D. Reed, Cincinnati, OH (US)

(73) Assignee: Intrexon Corporation, Blacksburg, VA (US)

( * ) Notice: Subject to any disclaimer, the term of this patent is extended or adjusted under 35 U.S.C. 154(b) by 178 days.

(21) Appl. No.: 10/724,532

(22) Filed: Nov. 29, 2003

(65) Prior Publication Data

US 2004/0203027 A1    Oct. 14, 2004

Related U.S. Application Data

(60) Provisional application No. 60/430,322, filed on Dec. 2, 2002.

(51) Int. Cl.
*C07K 14/00* (2006.01)
(52) U.S. Cl. ..................................... 530/300; 536/23.1
(58) Field of Classification Search ................ 530/300; 536/23.1
See application file for complete search history.

(56) References Cited

OTHER PUBLICATIONS

Kimura et al. 1997; J. Biol. Chem. 272(24): 15061-15064.*
Kimura et al. 1996; J. Biol. Chem. 271(36): 21726-21731.*
Haghighi et al. 2001; J. Biol. Chem. 276(26): 24145-24152.*

Ji, Yong, et al., Targeted Inhibition of Ca2+/Calmodulin-Dependent Protein Kinase II in Cardiac Longitudinal Sarcoplasmic Reticulum Results in Decreased Phospholamban Phosphorylation at Threonine 17, The Journal of Biological Chemistry, vol. 278, No. 27, Jul. 4, 2003, pp. 25063-25071, http://www.jbc.org.
Kimura, Y., et al., Phospholamban Domain I/Cytochrome $b_5$ Transmembrane Sequence Chimeras Do Not Inhibit SERCA2a, FEBS Letters 425 (1998) pp. 509-512.
Kimura, Y., et al., Phospholamban Inhibitory Function Is Activated By Depolymerization, The Journal of Biological Chemistry, 1997, vol. 272, No. 24, Issue of Jun. 13, pp. 15061-15064.
Kimura, Y., et al., Phospholamban Regulates the $Ca^{2+}$-ATPase through Intramembrane Interactions, The Journal of Biological Chemistry, 1996, vol. 271, No. 36, Issue of Sep. 6, pp. 21726-21731.

* cited by examiner

*Primary Examiner*—Karen Cochrane Carlson
(74) *Attorney, Agent, or Firm*—Daniel F. Nesbitt; Hasse & Nesbitt LLC

(57) ABSTRACT

The invention relates to targeting molecules to subcellular locations. In particular, the invention relates to compositions and methods to target molecules to the sarco(endo)plasmic reticulum (SR). The invention includes uses for polypeptide sequences as a localization signal to target therapeutic and experimental compounds or macromolecules to the SR of eukaryotic cells. The invention also includes nucleotide sequences encoding the polypeptide SR localization signal, allowing it to be incorporated into vectors for delivery of therapeutic or experimental gene products via in vitro or in vivo gene transfer.

20 Claims, 5 Drawing Sheets

SERCA2a  FLAG

SIGNAL FOR TARGETING MOLECULES TO THE SARCO(ENDO)PLASMIC RETICULUM

This application claims priority based on Provisional Patent Application 60/430,322 filed Dec. 2, 2002, before the USPTO, entitled "Signal for intracellular routing and localization of proteins to the sarco(endo)plasmic reticulum".

FIELD OF INVENTION

The invention relates to targeting molecules to subcellular locations. In particular, the invention relates to compositions and methods to target molecules to the sarco(endo)plasmic reticulum.

BACKGROUND AND PRIOR ART

The advent of sophisticated molecular biology techniques has conferred a greater understanding of the mechanisms of diseases, which has led to the design and synthesis of drugs that act at specific sites within cells. One example is antisense oligonucleotides, which must bind to specific target mRNAs in the cytoplasm or nucleus of diseased cells. See Lebedeva et al, 2000, Eur. J. Pharm. Biopharm. 50(1) 101–119 and Crooke, 1999, Biochem. Biophys. Acta 1489 (1)31–44. Delivery of the drug to the target site is paramount, as even the most potent drug will be ineffective if it cannot interact with its target. The simplest path by which drugs enter cells is diffusion. It has long been accepted that diffusion through a plasma or organelle membrane is restricted to small molecules, which is a major reason why most therapeutics are small molecules. See Foster et al, 1988, Biochim. Biophys. Acta 947(3)465–491. Thus, the requirement for the delivery of drugs to specific sites is contrary to the nature of high-molecular-weight (HMW) drugs and polymer carriers. However, even small diffusible drugs may not affect their target sites within cells. Disadvantages of drugs entering cells by diffusion include a requirement of high permeability and possible efflux (e.g., multidrug resistance due to the efflux of drugs by membrane pumps such as P-glycoprotein). See Kipecek, et al, 2000, Eur. J. Phar. Biophar. 50(1)61–81; Ryser et al, 1978, Proc. Natl. Acad. Sci. 75(4)3867–3870; and Ohkawa et al, 1993, Cancer Res. 53(18)4238–4242.

The large size and potential charge of HMW compounds prevents them from entering as many compartments as small molecules. See de Duve et al, 1974, Biochem. Pharmacol. 23(18)2495–2531. The biodistribution of small molecules is principally governed by their permeability and affinity for biological components with diffusion being their typical method of entry into biological compartments. If the desired balance in solubility and permeability of small drug molecules can be obtained by chemical modification, the drug should be able to reach most compartments and interact with its target. In contrast to small molecules, HMW material is internalized by endocytosis. Adding ligands to macromolecules can target the compound to specific cells, and thereby result in increased uptake, but once the material has been endocytosed, it still remains separated from the cell's interior by a biological membrane.

The most common fate of endocytosed material is delivery to the lysosome, where high levels of lysosomal enzymes are present. Drugs sensitive to these enzymes will be quickly degraded if steps are not taken to protect them or to facilitate their escape into the cytosol. The limited number of compartments accessible to macromolecules and probably exposure to a lower pH and degradative enzymes decreases their probability of success. Delivery of these and other HMW compounds to their target site is currently one of the greatest obstacles for their success. Since many drugs today are being designed to work at specific sites within cells, it would be very desirable to improve their delivery to the desired subcellular compartment. See Jensen et al, J. Controlled Release 87(2003)89–105.

The contractile apparatus in muscle cells, known as the sarcomere, is surrounded by a specialized membrane-bound sub-cellular structure called the sarcoplasmic reticulum (SR). There is a fundamental need to better understand SR protein interactions as well as develop therapies that act directly on SR-resident proteins. Therefore, a means is needed for targeting molecules to the SR as either a research tool or a therapeutic delivery system. One potential solution would be to use a component of an SR-resident protein as a targeting signal.

Intracellular calcium pools are maintained within the SR. Gradients of intracellular calcium control diverse biological activities, including muscle contraction. A class of proteins termed Sarco(endo)plasmic recticulum Calcium ATPases (SERCAs) are responsible for pumping calcium into the SR. Alterations in SERCA activity are associated with numerous disease states, including Darier disease and cardiac failure. Alterations in SERCA activity can be caused by changes in transcriptional or post-transcriptional regulation of SERCA gene expression, biochemical modification of a SERCA protein, and/or biophysical interactions of a SERCA protein with other proteins.

The SR-localized protein phospholamban (PLN) interacts with SERCA via biophysical associations. PLN is a 52-amino acid polypeptide with three domains, known as Ia, Ib, and II (Fujii et al, 1987, J. Clin. Invest. 79, 301–304). Conservation of PLN polypeptide sequence between mouse and human genes is 100%. There is a single amino acid substitution at amino acid 2 in canine and porcine compared to murine and human. PLN domain Ia (amino acid 1–20) is highly charged and helical, domain Ib (amino acid 21–30) is polar and unstructured, while domain II (amino acid 31–52) is neutrally-charged, very hydrophobic, and assumes an alpha-helical structure in a physiological milieu (Mortishire-Smith et al, 1995, Biochem. 34, 7603–7613). Further studies of domain II showed that the alpha-helix forms a transmembrarie domain that spans the lipid bilayer membrane of the SR. Biologically active PLN is a homopentamer of 5 PLN polypeptides. Experiments in cultured cells showed that the transmembrane domain of PLN associates with SERCA and inhibits calcium uptake into the SR (Kimura et al, 1996, J. Biol. Chem. 271, 21726–21731).

Further work studied mutations in individual amino acids in the PLN transmembrane domain to determine their effects on SERCA function (Kimura et al, 1997, J. Biol. Chem. 272, 15061–15064). In these studies, 22 different expression constructs were made with a single amino acid mutation of the transmembrane domain in each, so that each amino acid was changed to alanine in one of the constructs. Each mutant construct was transfected into mammalian cells, along with expression constructs for a SERCA protein, and SERCA function was assayed in each. While 14 of the mutations either maintained or increased inhibition of SERCA, 8 of the mutations abolished the ability of the PLN transmembrane domain to inhibit SERCA-driven calcium pumping.

While Kimura demonstrated that a single mutation to cause substitution of alanine for L31, N34, F35, I38, L42, 148, V49, or L52 (amino acid residues within the polypeptide of the transmembrane domain) disrupts inhibition of SERCA function in vitro, there has been no report of any successful application of this concept to conduct a protein to the SR. The nature of biological systems makes it difficult to predict accurately whether a mutated PLN transmembrane domain would in fact allow targeting of compounds or macromolecules to the SR. Thus, it remains unclear whether a mutant PLN transmembrane domain can serve as an SR targeting signal for a therapeutic or experimental compound or macromolecule without interferring with normal cellular functions, especially those associated with the SR.

DETAILED DESCRIPTION OF DRAWINGS

DETAILED DESCRIPTION OF POLYPEPTIDE AND NUCLEOTIDE SEQUENCES

Figure 1:
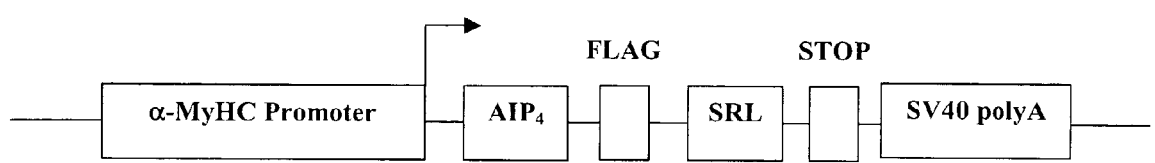
FIG. 1 shows a map of the α-MHC-AIP$_4$-SRL transgene construct.

SEQ ID NO:1 shows a fragment of native mouse or human phospholamban polypeptide comprising the transmembrane domain from amino acid residues 23–52.

SEQ ID NO:2 shows a mutated phospholamban polypeptide transmembrane structure with alanine substituted for residues L31 and N34.

SEQ ID NO:3 shows the sense strand of the nucleotide sequence encoding a mutated transmembrane domain of mouse or human phospholamban.

SEQ ID NO:4 shows the anti-sense strand of the nucleotide sequence encoding a mutated transmembrane domain of mouse or human phospholamban of SEQ ID NO:2.

SEQ ID NO:5 shows the sense strand of the nucleotide sequence encoding a mutated transmembrane domain of mouse or human phospholamban of SEQ, flanked by random nucleotides and restriction endonuclease sites.

SEQ ID NO:6 shows the anti-sense strand of the nucleotide sequence encoding a mutated transmembrane domain of mouse or human phospholamban, flanked by random nucleotides and restriction endonuclease sites.

SEQ ID NO:7 shows the amino acid sequence of an amino acid product produced by the nucleotide sequences encoding a AIP polypeptide.

SEQ ID NO:8 shows the amino acid sequence of a FLAG epitope.

SEQ ID NO:9 shows the sequence of an α-MHC-specific primer.

SEQ ID NO:10 shows the sequence of an AIP$_4$-specific primer.

BRIEF DESCRIPTIONS OF THE INVENTION

The invention is a polypeptide sequence comprising the amino acid sequence of SEQ ID NO:1, with at least one amino acid substitution at a location selected from the group consisting of L31, N34, F35, I38, L42, I48, V49, and L52. The substitution can be made using a non-hydrophobic amino acid. The nonhydorphobic amino acid substitute can be alanine or glycine, or any combination thereof, at any or all of the locations. The preferred locations for substitutions are at L31 and N34. The preferred amino acid substitute is alanine. The polypeptide of the invention can be linked to a compound or macromolecule and used to target the compound or macromolecule to a sarco(endo)plasmic region of a cell.

The invention is also a nucleic acid comprising a nucleotide sequence encoding the polypeptide sequence of SEQ ID NO:1 with at least one codon substitution encoding an amino acid substitution at an amino acid location selected from the group consisting of Leu-9, Asn-12, Phe-13, Ile-16, Leu-20, Ile-26, Val-27, and Leu-30; which correspond to phospholamban locations. L31, N34, F35, I38, L42, I48, V49, and L52. The codon substitution encodes a nonhydrophobic amino acid. The nonhydrophobic amino acid encoded can be alanine and glycine. The nucleic acid can be flanked by nucleotide sequences comprising restriction endonuclease sites and random nucleotides needed for restriction endonuclese activity. The nucleic acid of the invention can be linked to a second nucleotide sequence encoding a protein to be targeted to a sarco(endo)plasmic region of a cell.

DETAILED DESCRIPTION OF THE INVENTION

Abbreviations used in the description of this invention include:
α-MHC alpha-myosin heavy chain
AIP$_4$ SERCA2 activity inhibitor polypeptide 4
CAMKII calcium calmodulin kinase II
CMV human cytomegalovirus
FLAG™ Tradename for antigenic epitope (Kodak; Rochester, N.Y.)
HMW high molecular weight
NTG nontransgenic
PLN phospholamban
RyR ryanidine receeptor
SERCA sarco(endo)plasmic reticulum calcium ATPase
SR sarco(endo)plasmic reticulum
SRL SR localization signal
TG transgenic The present invention describes the composition and methods for use of a mutated form of the mouse PLN transmembrane domain as a targeting signal for a compound or macromolecule. Mutations in the transmembrane domain sequences prevent inhibition of SERCA function, while simultaneously maintaining SR-localization ability, demonstrating its utility as a signal for subcellular routing and localization of compounds or macromolecules, such as proteins, to the SR.

To create an SR localization signal (SRL), one or more of the amino acids encoding the mouse PLN transmembrane domain are changed to encode a non-hydrophobic amino acid, such as but not limited to alanine or glycine. Other nonhydorphobic amino acids can also be used to substitute for the native amino acid residues. The amino acid sequence of the wild-type mouse and human PLN transmembrane domain is: $Q^{23}$-$A^{24}$-$R^{25}$-$Q^{26}$-$N^{27}$-$L^{28}$-$Q^{29}$-$N^{30}$-$L^{31}$-$F^{32}$-$I^{33}$-$N^{34}$-$F^{35}$-$C^{36}$-$L^{37}$-$I^{38}$-$L^{39}$-$I^{40}$-$C^{41}$-$L^{42}$-$L^{43}$-$L^{44}$-$I^{45}$-$C^{46}$-$I^{47}$-$I^{48}$-$V^{49}$-$M^{50}$-$L^{51}$-$L^{52}$, also shown in SEQ ID:1where the amino acids are now numbered 1 through 30, rather than 23 through 52. Numbering of amino acid residues is based on their positions in the native, full-length polypeptide. Amino acid residues to be replaced are selected from the group comprising L31, N34, F35, I38, L42, I48, V49, and L52 which correspond Leu-9, Asn-12, Phe-13, Ile-16, Leu-20, Val-27, and Leu-30 of SEQ ID NO:1. The preferred embodiment contains substitution of alanine at both L31 and N34, however, other neutral amino acid substitutions may be made at either of these sites, or at F35, I38, L42, V49, or L52 which correspond to Phe-13, Ile-16, Leu-20, Ile-26, Val-27, and Leu-30 of SEQ ID NO:1. The preferred amino acid sequence is shown in SEQ ID:2. Leu-9 and Asn-12 of SEQ ID NO:2, which correspond to L31 and N34 are chosen for substitution on the basis of their location in the phospholamban pentamer that places them in apposition to SERCA. Substitution of these 2 amino acids disrupts the interaction between SERCA and phospholamban, preventing inhibition of SERCA function. This SRL can be synthesized de novo using any state-of-the-art amino acid synthesizer, commonly found in commercial protein production facilities. The SRL polypeptide can then be linked to a therapeutic or experimental compound or macromolecule for administration to human subjects or animals, or for treatment of in vivo cell cultures or tissue explants. Such linkage can include but is not limited to covalent or enzymatic linkage.

Alternatively, a mutated transmembrane domain can be encoded in a nucleotide sequence to produce an SRL. Single nucleotide substitutions can be made at the desired locations by changing an amino acid codon with the nucleotide sequence. Any number of amino acid substitutions can be made, and any amino acid substitution desired can be encoded. Each strand of a double-stranded DNA molecule encoding an SRL can be synthesized independently, and used in a variety of ways that will be described herein. Examples of nucleotide sequences encoding sense and antisense strands of a preferred SRL are provided in SEQ ID:3 and SEQ ID:4.

Additional sequences can be added to the flanking regions of the SRL to encode convenient restriction endonuclease sites. These restriction sites can be used to facilitate cloning of the SRL into a cloning vector. The restriction sites flanking the transmembrane domain core sequences can include, but are not limited to any of the commonly used sites in most commercially available cloning vectors. Examples of such sites are those recognized by BamHI, ClaI, EcoRI, EcoRV, SpeI, AflII, NdeI, NheI, XbaI, XhoI, SphI, NaeI, SexAI, HindIII, HpaI, and PstI restriction endonucleases. Sites for cleavage by other restriction enzymes, such as homing endonucleases can also be used for this purpose. It is preferred that the first and second restriction sites differ from each other, so that the double-stranded DNA molecule encoding the SRL can be directionally cloned into corresponding complementary sites of any suitable cloning vector.

An example of how the nucleotide sequences encoding an SRL can be produced is as follows. Complimentary oligonucleotides encoding the SRL flanked by restriction endonuclease sites are synthesized and annealled. The ends of the resulting double-stranded molecule are cleaved using the appropriate restriction endonuclease enzymes, and the SRL-encoding DNA fragment is inserted into a cloning vector. When the SRL is placed in-frame adjacent to sequences within a transgenic gene construct that will be translated into a protein product, it will be part of a fusion protein when expressed in a cell or a transgenic animal. The fusion protein can be directed toward either the inward or outward face of the SR membrane by orienting the amino-or carboxy-terminus relative to the orientation of the nucleotide sequences encoding the gene of interest. For example, sequences encoding a auto-inhibitory polypeptide that inhibits CAM-Kinase II ($AIP_4$) were organized within a transgene construct such that the $AIP_4$ sequences were followed by SRL encoding-sequences, all oriented in the 5'-3' direction. When this construct was used to generate transgenic mice, the expressed transgenic protein comprised the $AIP_4$ fused to SRL ($AIP_4$-SRL). $AIP_4$-SRL was localized to the outward face of the SR.

Since PLN is highly conserved between mammals, the same sequences used in mouse can be used in humans to target therapies to myocardiocytes. Targeted therapies can include delivery of expressed and purified recombinant protein with an SRL. In addition, gene delivery via adenovirus, lentivirus, adeno-associated virus, or other viral constructs that include an SRL targeting signal in the expressed protein product.

EXAMPLE 1

A polypeptide sequence comprising an SRL and a FLAG™ epitope are synthesized. The polypeptide is solubilized in media that is added to PC12 cells cultured on cover slips. The polypeptide is endocytosed by the PC12 cells, and transported to the endoplasmic reticulum. Six hours after treatment with the polypeptide, the media is removed and cells are fixed to the coverslips. Immunohistochemical staining is performed using an anti-FLAG™ antibody. The FLAG™ epitope is detected in a region that is consistent with localization to the endoplasmic reticulum in the PC12 cells.

EXAMPLE 2

A transgene is constructed using a human cytomegalovirus (CMV) heterologous promoter to direct expression of a GFP-SRL fusion protein. The transgene is transiently transfected into PC12 cells. After 48 hours, the cells are viewed by confocal microscopy. The GFP-SRL fusion protein is found localized to a discrete region of the endoplasmic reticulum.

EXAMPLE 3

A transgene construct is built to produce a protein product with expression driven by a CMV promoter. The transgene comprises a synthetic gene expression unit engineered to encode three functional domains. Each of these three functional domains is synthesized as a pair of complimentary oligonucleotides that are annealed in solution and then assembled in a cloning vector in consecutive steps. Starting at the amino-terminus, the expression unit contains nucleotide sequences that encode a CaMKII auto-inhibitory polypeptide (AIP), a FLAG™ epitope, and an SRL. The nucleotide sequences encoding the AIP polypeptide produces a 13 amino acid product (KKALRRQEAVDAL)(SEQ ID NO:7) known to be a highly specific and potent inhibitor of CaMKII. Nucleotide sequences encoding a FLAG epitope (amino acids DYKDDDDK)(SEQ ID NO:8) are placed 3' of those encoding AIP. Finally, nucleotide sequences encoding an SRL are placed 3' of those encoding the FLAG epitope. The nucleotide sequences used encode an SRL flanked at the 5' and 3' ends by HindIII and XhoI restriction sites, respectively. The restriction sites are flanked in turn by 6–9 random nucleotides to facilitate cleavage with HindIII and XhoI. The nucleotide sequences used in this example are shown in SEQ ID:5 and SEQ ID:6. The assembled gene expression unit is subsequently subcloned into a CMV expression vector and used to transiently transfect BHK-21 cells cultured on coverslips. After 48 hours following transfection, the media is removed and cells are fixed to the coverslips. Immunohistochemical staining is performed using an anti-FLAG™ antibody. The FLAG™ epitope is detected in a region that is consistent with localization to the endoplasmic reticulum in the BHK-21 cells.

EXAMPLE 4

In order to demonstrate the specific targeting of a protein to the SR in vivo, a transgene construct is used to generate mice with expression of a protein targeted to cardiac longitudinal SR. The transgene construct, incorporating use of an SRL of the present invention, is shown in FIG. 1. The transgene comprises a synthetic gene expression unit engineered to encode three functional domains. Each of these three functional domains are synthesized as complimentary oligonucleotides that are annealed in solution and then assembled in a cloning vector in consecutive steps. Starting at the amino-terminus, the expression unit contains nucleotides that encode a tetramer of AIP ($AIP_4$), a FLAG™ epitope, and an SRL. This expression unit is subsequently subcloned into a pBluescript-based vector (Stratagene; La Jolla, Calif.) between nucleotide sequences encoding a 5.5-kb region of the murine α-myosin heavy chain (α-MHC) promoter and an SV40 polyadenylation signal. The transgene (α-MHC-$AIP_4$-SRL) is injected into pronuclei of fertilized mouse oocytes. The resultant pups are screened for the presence of the transgene by PCR, using an α-MHC-specific primer (5'-GCCCACACCAGAAATGACAGA-3') (SEQ ID NO:9) and an $AIP_4$-specific primer (5'-ACTC-GAGCAGGAGCATGACGATA-3')(SEQ ID NO:10). Transgenic (TG) founder mice are bred with wild-type mice. Heterozygous TG animals from at least the third generation are used for the following experiments, with their non-transgenic (NTG) littermates serving as controls.

Figure 2:
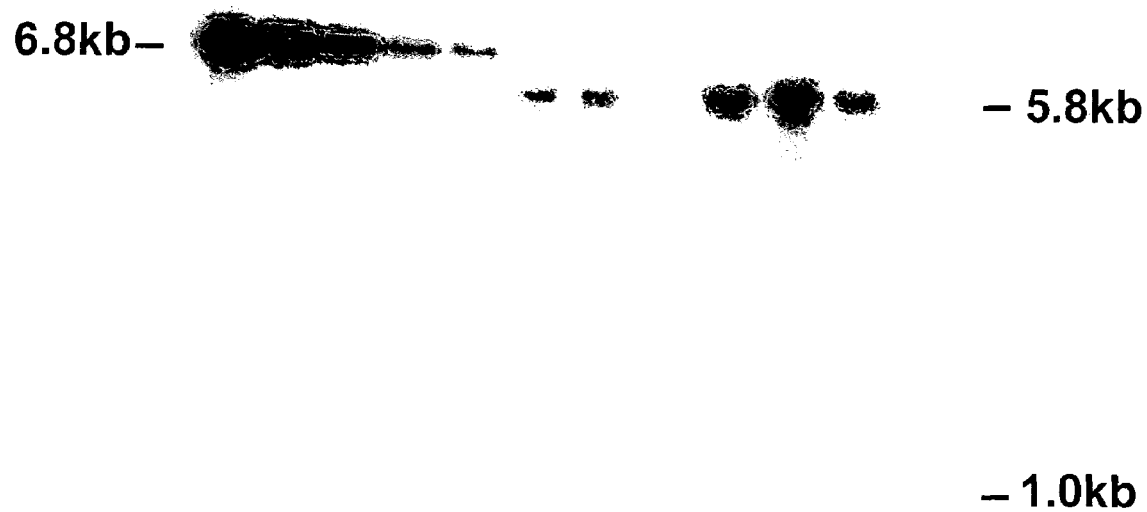
FIG. 2 shows a Southern blot determination of transgene copy number in TG mice.

Experiment 1: Southern blotting analysis is performed to determine the copy number, shown in FIG. 2. For each mouse tested, 10 μg of genomic DNA prepared from tail biopsies is digested with KpnI and electrophoresed. The blots are hybridized with a radio-labeled probe generated from the SalI/SalI fragment of the transgene. The probe detects 5.8 kb and 1 kb bands in lanes containing DNA from TG mice, but not NTG. Intensities of the TG bands are measured using PhosphoImager (Molecular Dynamics) and compared with the transgene Plasmid control bands to estimate copy number. This experiment demonstrates that mice in Example 4 harbor the α-MHC-$AIP_4$-SRL transgene in their genomes.

Figure 3:
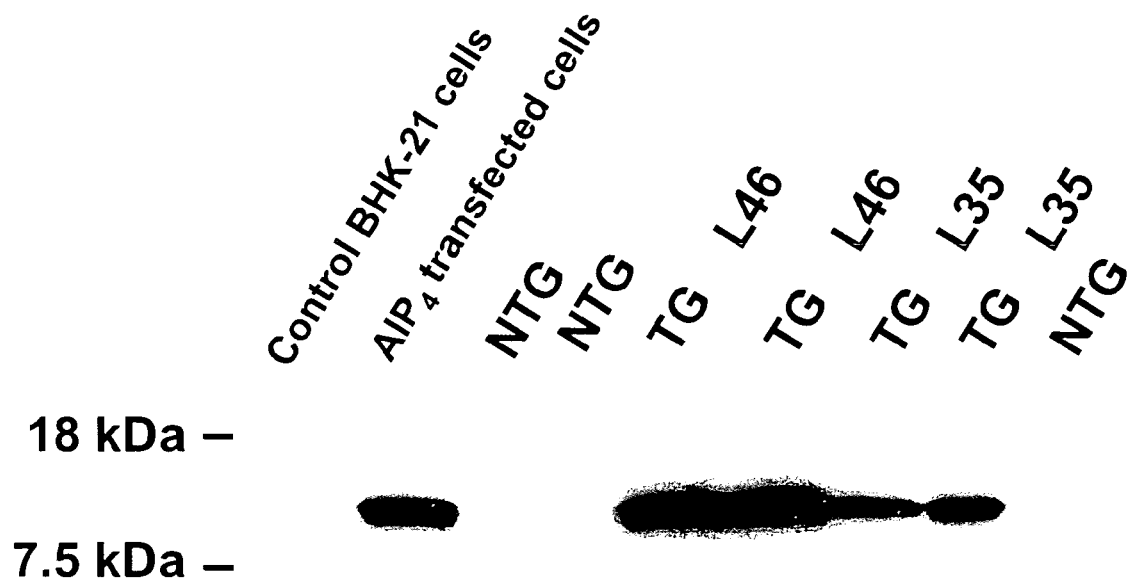
FIG. 3 shows a Western blot of FLAG™ expression in whole heart homogenates from TG mice.
Figure 4:
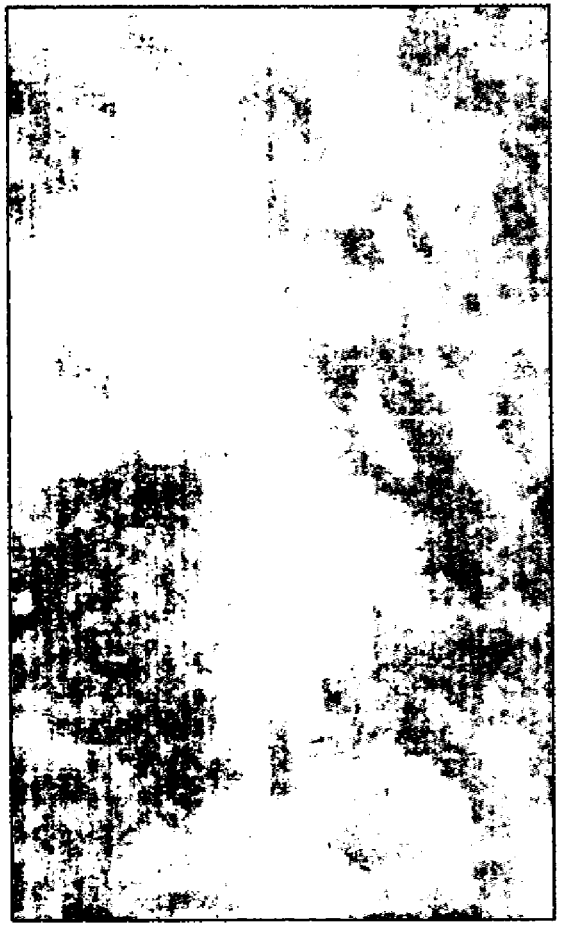
FIG. 4 shows localization of FLAG™ and SERCA expression in a TG mouse heart.
Figure 4:
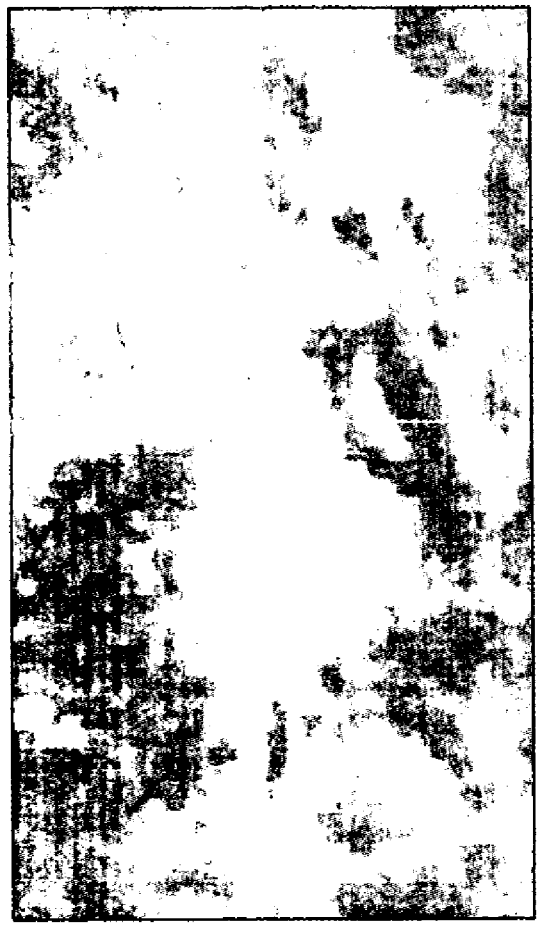

Experiment 2: Cardiac homogenates are prepared for Western blot analysis as described by Ji et al, 2000, J. Biol. Chem. 275:38073–38080. Western blot analysis of FLAG™ expression in transgenic hearts is shown in FIG. 3. Enhanced chemiluminescence is performed using the SuperSignal Chemiluminescent Detection System (Amersham). Calsequestrin protein is used as internal control. The data are analyzed using Intwin 4.0. A DNA construct of AIP-FLAG-SRL driven by CMV promoter was used to transient transfect BHK-21 cells and served as positive control. This experiment demonstrates that the α-MHC-$AIP_4$-SRL transgene is expressed in the cardiac tissue of TG mice, with FLAG™ protein detected in TG but not NTG protein homogenates. Quantitation of the FLAG™ protein shows 2–3 fold higher levels in line 46 than in line 35 TG mice. Experiment 3: Whole hearts are taken from TG and NTG mice. Hearts are coated with Tissue-Tek OCT compound and immediately frozen in liquid $N_2$. Frozen tissue sections 4 microns thick are stained as described by Morgan et al, 1991, N. Eng. J. Med. 325:625–632. FLAG™ expression is detected using mouse anti-FLAG antibody (1:10 dilution) followed by fluorescein isothiocyanate-conjugated goat anti-mouse IgG antibody (1:200 dilution). The same tissue section is used to detect SERCA2a protein using polyclonal anti-SERCA2a antibody (1:200 dilution) followed by fluorescein Cy-3-conjugated goat anti-rabbit IgG antibody (1:200 dilution). The tissue sections are examined using a Nikon 135 optiphot fluorescence microscope. To confirm that $AIP_4$-FLAG is targeted to the cardiac SR in TG mice, tissue sections are immunofluorescently stained with an antibody to SERCA2a, which is expressed only in SR, and anti-FLAG, shown in FIG. 4. Expression patterns of FLAG and SERCA2a are indistinguishable, demonstrating that the $AIP_4$-FLAG protein is targeted to the SR. Sections are also immunofluorescently stained pairing anti-FLAG with other SR-specific antibodies, including anti-calsequestrin polyclonal antibody (Swant, Switzerland); monoclonal anti-PLB, anti-RyR (Affinity Bioreagents. Inc.), and anti-SERCA2a antibody (Dr. Frank Wyutack. Results are indistinguishable with those pairing anti-FLAG and anti-SERCA2a. Immunofluorescent staining with antibodies to anti-FLAG and anti-CaMKII-δ, a cytosolic protein, is found in distinct patterns that do not overlap significantly. This histological experiment demonstrates that the $AIP_4$-FLAG protein was localized to the SR.

Figure 5:
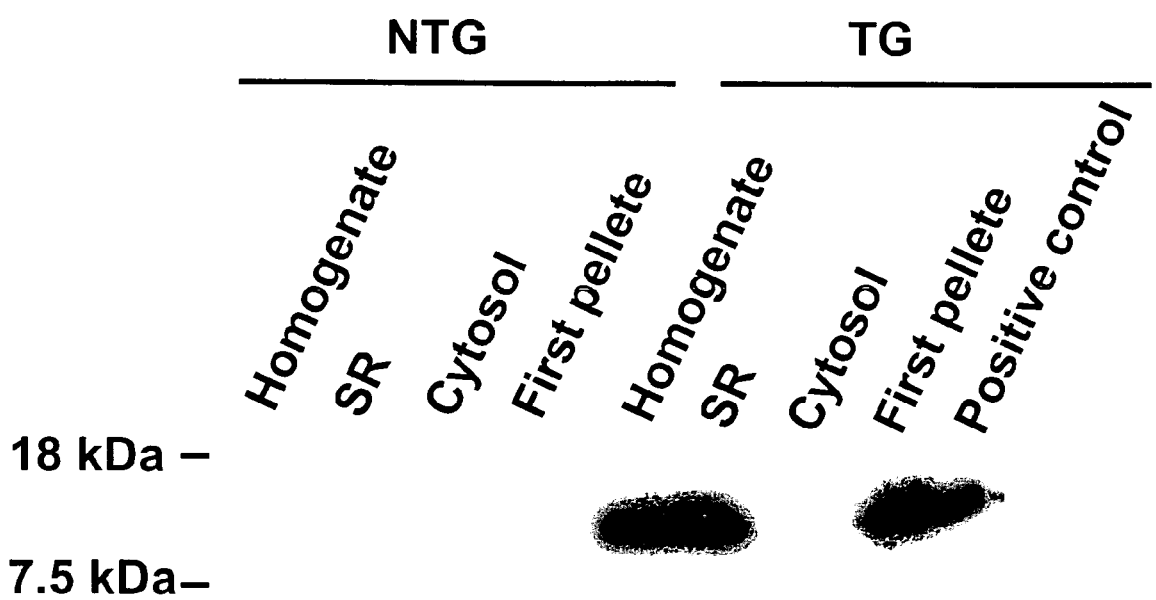
FIG. 5 shows a Western blot of FLAG™ protein levels in homogenates and subcellular fractions from NTG and TG hearts.

Experiment 4: Hearts are harvested from 10 NTG and 10 TG mice as described for Experiment 2, above. Whole heart homogenates, cytosolic fractions, SR-enriched microsome subcellular fractions, and first pellete fractions are immunoblotted with SR- and cytosol-specific antibodies. Immunoblotting with SR-specific antibodies (anti-calsequestrin, anti-PLB, anti-RyR, and anti-SERCA2a) produced bands in lanes containing TG and NTG whole heart homogenates and microsome fractions, but not cytosolic and first pellete fractions. Anti-FLAG antibodies produced a band in the same fractions as SR-specific antibodies, but only in TG hearts, shown in FIG. 5. These findings are distinct from those using anti-CaMKII-δ antibodies, found in NTG and TG whole heart homogenates and cytosol fractions, but not in microsome fractions. This experiment demonstrates that $AIP_4$-FLAG protein is found in the SR-containing fraction, but not in the cytosol-containing fraction, confirming that the SRL targeted the $AIP_4$-FLAG protein to the SR.

These examples demonstrate the utility of an SRL to target delivery of therapeutic or experimental compounds or macromolecules to the SR. Polypeptide SRLs can be linked to compounds or macromolecules to treat diseased muscle or cardiomyocytes and administered orally or parenterally in table, capsule, or liquid form, intranasal or inhaled aerosol, subcutaneous, intramuscular, intraperitoneal, or other injection; intravenous instillation; or any other clinical routes of administration. Furthermore, the nucleotide sequences encoding the SRL allow it to be incorporated into a vector designed to deliver a gene product to a cell in which it is desirable to target that gene product to the SR. Such vectors include plasmids, cosmids, artificial chromosomes, and genetically-modified viruses. Delivery can be accomplished in vivo or in vitro to eukaryotic cells. It can be envisioned that some delivery methods would include isolation of the intended recipient's cells or donor cells and delivery of the vector to those cells, followed by treatment of the recipient with the cells.

What is claimed is:

1. An isolated polypeptide comprising the amino acid sequence of SEQ ID NO:1 with at least two amino acid substitutions at two locations selected from the group consisting of Leu-9, Asn-12, Phe-13, Ile-16, Leu-20, Ile-26, Val-27, and Leu-30.

2. The isolated polypeptide of claim 1, wherein the substitutions are with a non-hydrophobic amino acid.

3. The isolated polypeptide of claim 1, wherein the substitutions are with an amino acid selected from the group consisting of alanine and glycine.

4. The isolated polypeptide of claim 3, wherein substitutions are made at Leu-9 and Asn-12.

5. The isolated polypeptide of claim 1, wherein the polypeptide is linked to a compound to be targeted to a sarco(endo)plasmic region of a cell.

6. The isolated polypeptide of claim 1, wherein the polypeptide is linked to a macromolecule to be targeted to a sarco(endo)plasmic region of a cell.

7. The isolated polypeptide of claim 4, wherein the polypeptide is linked to a macromolecule or compound to be targeted to a sarco(endo)plasmic region of a cell.

8. An isolated polypeptide comprising the amino acid sequence of SEQ ID NO:2.

9. The isolated polypeptide of claim 8, wherein the polypeptide is linked to a compound to be targeted to a sarco(endo)plasmic region of a cell.

10. The isolated polypeptide of claim 8, wherein the polypeptide is linked to a macromolecule to be targeted to a sarco(endo)plasmic region of a cell.

11. An isolated nucleic acid comprising a nucleotide sequence encoding the polypeptide sequence of SEQ ID NO:1 with at least two codon substitutions encoding an amino acid substitution at two amino acid locations selected from the group consisting of Leu-9, Asn-12, Phe-13, Ile-16, Leu-20, Ile-26, Val-27, and Leu-30.

12. The isolated nucleic acid of claim 11, wherein the codon substitutions encodes a non-hydrophobic amino acid.

13. The isolated nucleic acid of claim 11, wherein the codon substitutions encodes an amino acid selected from the group consisting of alanine and glycine.

14. The isolated nucleic acid of claim 11, wherein the nucleotide sequence is linked to a second nucleotide sequence encoding a protein to be targeted to a sarco (endo)plasmic region of a cell.

15. An isolated nucleic acid comprising a nucleotide sequence selected from nucleotide sequences represented by SEQ NO:3, SEQ ID NO:4, SEQ ID NO:5, and SEQ ID NO:6.

16. The isolated nucleic acid of claim 15, wherein when the nucleotide sequence is selected from SEQ ID NO:3 and SEQ ID NO:5, the nucleotide sequence is linked to a second nucleotide sequence encoding a protein to be targeted to a sarco(endo)plasmic region of a cell; and wherein when the nucleotide sequence is selected from SEQ ID NO:4 and SEQ ID:6, the nucleotide sequence is linked to a third nucleotide sequence, wherein the third nucleotide sequence is a compliment of a polynucleotide that encodes a protein to be targeted to a sarco(endo)plasmic region of a cell.

17. A method for targeting a compound or a macromolecule to the sarco(endo)plasmic region of a cell, the method comprising the steps of:

(1) providing an isolated polypeptide comprising the amino acid sequence of SEQ ID NO:1 with at least one amino acid substitution at a location selected from the group consisting of Leu-9, Asn-12, Phe-13, Ile-16, Leu-20, Ile-26, Val-27, and Leu-30;

(2) linking the polypeptide to a compound or macromolecule to provide a linked compound or linked macromolecule;

(3) administering the polypeptide-linked compound or polypeptide-linked macromolecule to cells.

18. The method of claim 17, wherein the substitution is made with a non-hydrophobic amino acid.

19. The method of claim 17, wherein the substitution is made with an amino acid selected from the group consisting of alanine and glycine.

20. The method of claim 17, wherein substitutions are made at Leu-9 and Asn-12.

* * * * *

SEQUENCE LISTING

<160> NUMBER OF SEQ ID NOS: 6

<210> SEQ ID NO 1
<211> LENGTH: 30
<212> TYPE: PRT
<213> ORGANISM: Mus musculus

<400> SEQUENCE: 1

Gln Ala Arg Gln Asn Leu Gln Asn Leu Phe Ile Asn Phe Cys Leu Ile
1               5                   10                  15

Leu Ile Cys Leu Leu Leu Ile Cys Ile Ile Val Met Leu Leu
            20                  25                  30

<210> SEQ ID NO 2
<211> LENGTH: 30
<212> TYPE: PRT
<213> ORGANISM: mus musculus

<400> SEQUENCE: 2

Gln Ala Arg Gln Asn Leu Gln Asn Ala Phe Ile Ala Phe Cys Leu Ile
1               5                   10                  15

Leu Ile Cys Leu Leu Leu Ile Cys Ile Ile Val Met Leu Leu
            20                  25                  30

<210> SEQ ID NO 3
<211> LENGTH: 108
<212> TYPE: DNA
<213> ORGANISM: mus musculus

<400> SEQUENCE: 3
atgcatgaga gaaggcctca ggccaggcag aacctccaga atgctttcat tgcttttgt      60 ctgattctca tctgcctcct gctgatttgc attatcgtca tgctcctg               108

<210> SEQ ID NO 4
<211> LENGTH: 108
<212> TYPE: DNA
<213> ORGANISM: mus musculus

<400> SEQUENCE: 4
caggagcatg acgataatgc aaatcagcag gaggcagatg agaatcagac aaaaagcaat     60
gaaagcattc tggaggttct gcctggcctg aggccttctc tcatgcat                108

<210> SEQ ID NO 5
<211> LENGTH: 135
<212> TYPE: DNA
<213> ORGANISM: mus musculus

<400> SEQUENCE: 5
gagagaaagc ttatgcatga gaaggcct caggccaggc agaacctcca gaatgctttc       60
attgcttttt gtctgattct catctgcctc ctgctgattt gcattatcgt catgctcctg    120
ctcgaggaga gagag                                                     135

<210> SEQ ID NO 6
<211> LENGTH: 135
<212> TYPE: DNA
<213> ORGANISM: mus musculus

<400> SEQUENCE: 6
ctctctctcc tcgagcagga gcatgacgat aatgcaaatc agcaggaggc agatgagaat     60

-continued

```
cagacaaaaa gcaatgaaag cattctggag gttctgcctg gcctgaggcc ttctctcatg    120
cataagcttt ctctc                                                     135
```